US00PP15422P2

(12) United States Plant Patent
Boeder

(10) Patent No.: US PP15,422 P2
(45) Date of Patent: Dec. 14, 2004

(54) ***CHRYSANTHEMUM* PLANT NAMED 'KEPA'**

(50) Latin Name: *Chrysanthemum morifolium*
Varietal Denomination: Kepa

(75) Inventor: Mark Roland Boeder, The Hague (NL)

(73) Assignee: Chrysanthemum Breeders Association, N.V. (NL)

( * ) Notice: Subject to any disclaimer, the term of this patent is extended or adjusted under 35 U.S.C. 154(b) by 3 days.

(21) Appl. No.: 10/756,372

(22) Filed: Jan. 14, 2004

(51) Int. Cl.[7] ..... A01H 5/00
(52) U.S. Cl. ..... Plt./293
(58) Field of Search ..... Plt./293

*Primary Examiner*—Anne Marie Grunberg
*Assistant Examiner*—Annette H Para
(74) *Attorney, Agent, or Firm*—Parkhurst & Wendel, L.L.P.

(57) ABSTRACT

A *Chrysanthemum* plant named 'Kepa' characterized by its medium sized blooms with purple ray florets and prolific branching; natural season flower date September 8–13; blooming for a period of 5 weeks.

2 Drawing Sheets

BACKGROUND OF THE INVENTION

'Kepa' is a product of a breeding and selection program for outdoor pot mums (garden mums) which had the objective of creating new *Chrysanthemum* cultivars with a decorative type flower, a natural season flower date around September 8–13; blooming for a period of 5 weeks. The new plant of the present invention comprises a new and distinct cultivar of *Chrysanthemum* plant 'Kepa' is a seedling resulting from the open pollination among groups of *Chrysanthemum* cultivars maintained under the control of the inventor for breeding purposes. The new and distinct cultivar was discovered and selected as one flowering plant by Mark Roland Boeder on a cultivated field in Rijsenhout Holland in September 2001. The plant has been asexually reproduced by cuttings in greenhouses at Rijsenhout Holland. The new cultivar has been found to retain its distinctive characteristics through successive propagations.

BRIEF DESCRIPTION OF THE DRAWINGS

The present invention of a new and distinct variety of *Chrysanthemum* is shown in the accompanying drawings, the color being as nearly true as possible with color photographs of this type.

DESCRIPTION OF THE INVENTION

Figure 1:
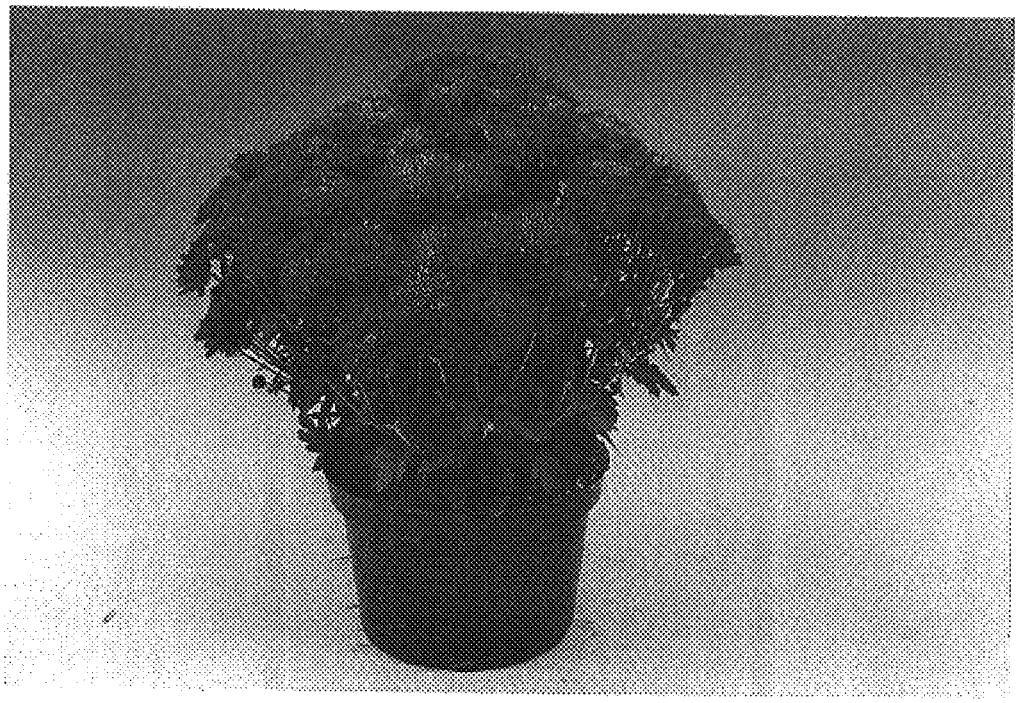
FIG. 1 shows a plant of the cultivar in full bloom.
Figure 2:
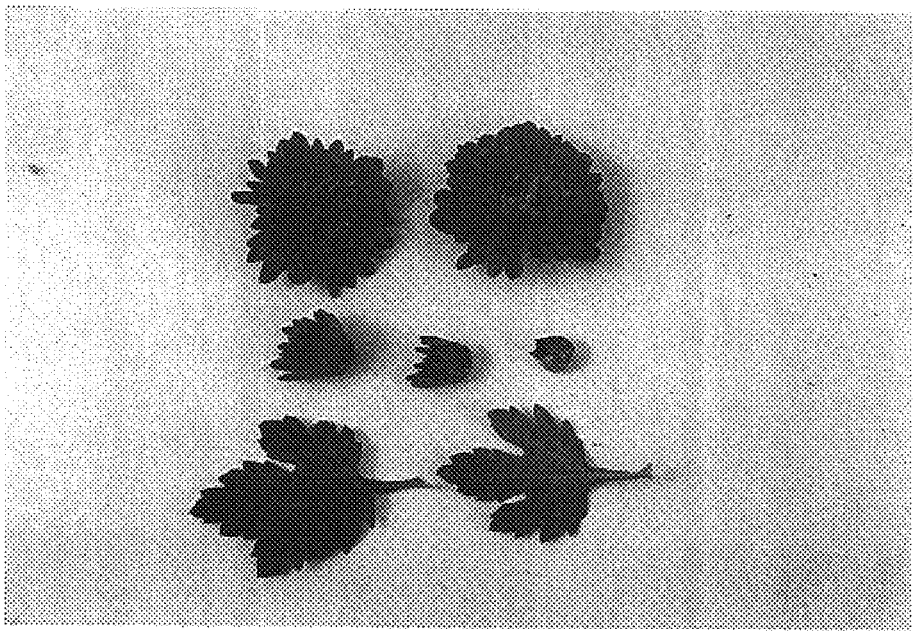
FIG. 2 shows the various stages of bloom and foliage of the new cultivar.

This new variety of *Chrysanthemum* is of the botanical classification *Chrysanthemum morifolium.* The observations and measurements were gathered from plants grown out door in Rijsenhout, Holland under natural day length and temperature and planted in week 23 in 2002. The natural blooming date of this crop was September 8–13 (week 37). The average height of the plant was 35 cms. No growth retardants were used. No tests were done on disease or insect resistance or susceptibility. No tests were done on cold or drought tolerance. This new variety produces medium sized blooms with purple ray florets blooming for a period of 5 weeks.

From the cultivars known to inventor the most similar existing cultivar in comparison to 'Kepa' is 'Venus' (U.S. Plant patent application Ser. No. 10/316,939). When 'Venus' and 'Kepa' are being compared the following differences are noticed: The differences of 'Vensu' and 'Kepa' are (1) Number of ray florets. 'Venus' has a smaller number of ray florets than 'Kepa'. (2) Longitudinal axis of majority of ray florets. This axis is in 'Venus' reflexing and in 'Kepa' straight.

The following is a description of the plant and characteristics that distinguish 'Kepa' as a new and distinct variety. The color designations are taken from the plant itself. Accordingly, any discrepancies between the color designations and the colors depicted in the photographs are due to photographic tolerances. The color chart used in this description is: The Royal Horticultural Society Colour Chart, edition 1995.

TABLE 1

Botanical Description of cultivar 'Kepa'

| | |
|---|---|
| Bud | |
| Size | Small; cross-section 1 cm, height 0.6 cm |
| Outside Color | Yellow-green 145C |
| Involucral bracts | 2 rows, length 7 mm, width 3 mm |
| Involucral bracts among disc-florets | Not present |
| Involucral bracts color | Green 138B |
| Bloom | |
| Type | Decorative |
| Size | Medium |
| Fully Expanded | 5 cm |
| Peduncle length | 8 cm |
| Peduncle color | Green 13B |
| Number of blooms per branch | Approx. 10 blooms per branch |
| Performance on the plant | 5 weeks |
| Seeds | Produced in small quantities, ovate grey-brown 199A, 1½ mm in length |
| Fragrance | Typical *chrysanthemum,* slightly |
| Color | |
| Center of the flower | Immature Red-purple 72A<br>Mature Yellow 13A |

TABLE 1-continued

| Botanical Description of cultivar 'Kepa' | |
|---|---|
| Color of upper surface of the ray-florets | Red-purple 58A |
| Color of the lower surface of the ray-florets | Red-purple 70A |
| Tonality from Distance | A garden mum with purple flowers |
| Color of the upper side of the ray florets after aging of the plant | Red-purple 58C |
| Ray florets | |
| Texture | Upper and under side smooth |
| Number | 160–180 |
| Cross-section | Flat |
| Longitudinal axis of majority | Straight |
| Length of corolla tube | 1 cm |
| Ray-floret margin | Entire |
| Ray-floret length | 2.1 cm |
| Ray-floret width | 0.8 cm |
| Ratio length/width | Medium |
| Shape of tip | Rounded |
| Disc florets | |
| Disc diameter | 0.2 cm |
| Distribution of disc florets | Few, only visible in mature bloom |
| Shape | Tubular |
| Color | Yellow-green 145C |
| Receptacle shape | Domed raised |
| Reproductive Organs | |
| Stamen | Present only in disc florets |
| Stamen color | Yellow-green 144A |
| Pollen | Produced in small quantity |
| Pollen color | Yellow 7A |
| Styles | Thin |
| Style color | Yellow 13A |
| Style Length | 3 mm |
| Stigma color | Yellow-green 144A |
| Stigma Width | 1 mm |
| Ovaries | Enclosed in calyx |
| Plant | |
| Form | A garden mum outdoor mounded and round |
| Growth habit | Spreading |
| Growth rate | Intermediate |
| Height | 35 cm |
| Width | 38 cm |
| Stem Color | Yellow-green 147C |
| Stem Strength | Strong |
| Stem Brittleness | Not brittle |
| Stem Anthocyanin Coloration | Absent |

TABLE 1-continued

| Botanical Description of cultivar 'Kepa' | |
|---|---|
| Intermode length | 2.5 cm |
| Length of lateral branch | From top to bottom 16 cm |
| Lateral branch color | Yellow-green 147C |
| Lateral branch, attachment | Strong |
| Branching (average number of lateral branches) | Good with 6–7 breaks after pinching |
| Natural season blooming date | September 8–13 |
| Foliage | |
| Leaf color | Upper side Green 139B<br>Under side Green 139C |
| Color midvein | Upper side Yellow-green 147D<br>Under side Yellow-green 148D |
| Size | Medium; length 5 cm, width 3 cm |
| Quantity (number per lateral branch) | 20–25 |
| Shape | Cordiform |
| Texture upper side | Glabrous |
| Texture under side | Pubescent |
| Venation arrangement | Palmate |
| Shape of the margin | Serrated |
| Shape of Base of Sinus Between Lateral Lobes | Rounded |
| Margin of Sinus Between Lateral Lobes | Diverging |
| Shape of Base | Obtuse |
| Apex | Mucronate |
| Petiole length | 0.8 cm |
| Petiole color | Yellow-green 147D |

TABLE 2

| Differences with the comparison varieties | | |
|---|---|---|
| | 'Kepa' | 'Venus' |
| Number of ray florets | 160–180 | 140–150 |
| Longitudinal axis of majority of ray florets | Straight | Reflexing |

I claim:

1. A new and distinct variety of *Chrysanthemum* plant as described and illustrated.

* * * * *